United States Patent [19]
Nesbitt

[11] Patent Number: 4,899,736
[45] Date of Patent: * Feb. 13, 1990

[54] OPTIONALLY DISPOSABLE CERVICAL RESTRAINING DEVICE

[76] Inventor: William R. Nesbitt, 6967 Blue Oak La., Loomis, Calif. 95650

[*] Notice: The portion of the term of this patent subsequent to Jun. 17, 2003 has been disclaimed.

[21] Appl. No.: 93,610

[22] Filed: Sep. 8, 1987

Related U.S. Application Data

[63] Continuation-in-part of Ser. No. 871,390, Jun. 6, 1986, Pat. No. 4,718,412, which is a continuation-in-part of Ser. No. 650,206, Sep. 13, 1984, Pat. No. 4,594,999.

[51] Int. Cl.$^4$ .................................................. A61F 5/04
[52] U.S. Cl. .................................. 128/87 R; 128/87 B; 128/870
[58] Field of Search ..................... 128/87 R, 87 B, 88, 128/78, 869, 870, 85

[56] References Cited

U.S. PATENT DOCUMENTS

| | | | |
|---|---|---|---|
| 2,409,195 | 10/1946 | Crawford | 128/87 R |
| 3,732,863 | 5/1973 | Harrington | 128/84 C |
| 3,850,167 | 11/1974 | Seeley | 128/87 R |
| 4,211,218 | 7/1980 | Kendrick | 5/82 R X |
| 4,528,981 | 7/1985 | Behar | 5/437 X |
| 4,589,407 | 5/1986 | Koledin et al. | 128/88 X |
| 4,593,788 | 6/1986 | Miller | 128/870 X |

Primary Examiner—Robert A. Hafer
Assistant Examiner—Kevin G. Rooney
Attorney, Agent, or Firm—Mark C. Jacobs

[57] ABSTRACT

An optionally disposable lightweight, readily stored, low cost cervical spine board made of plastic corrugated board. The device has pre-cut score lines therein for folding the device around the sides of the head and around the sides of the body.

Head and neck tabs, and body wings are secured by straps which straps are pre-attached to the device, and which are secured by conventional lock closures similar to those used in car seat belts and other restraining devices.

22 Claims, 2 Drawing Sheets

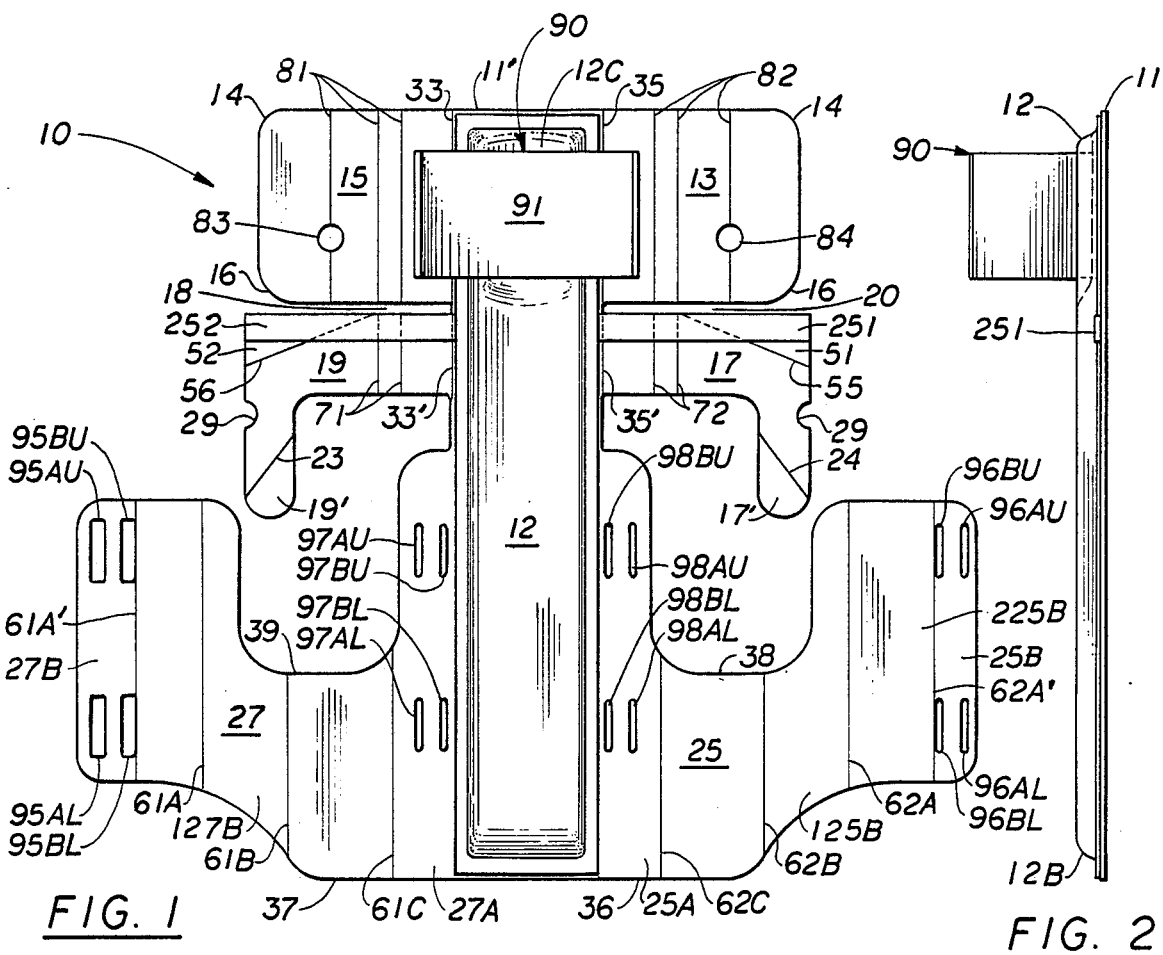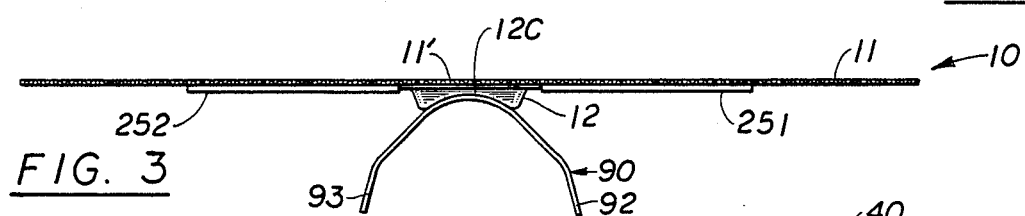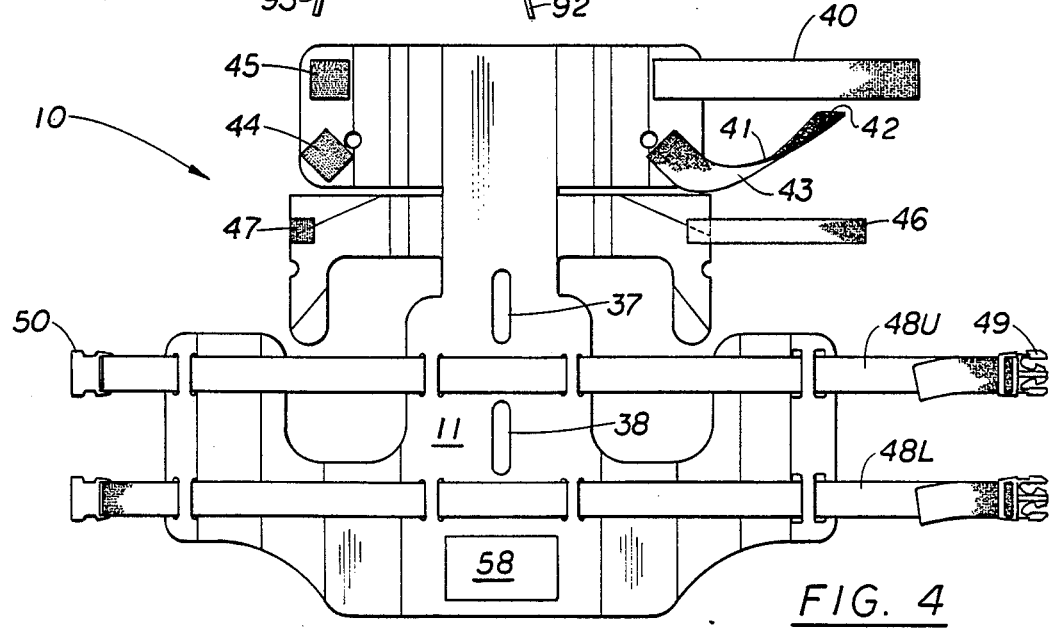

4,899,736

OPTIONALLY DISPOSABLE CERVICAL RESTRAINING DEVICE

RELATION TO OTHER APPLICATIONS

This application is a continuation in part of my copending application Ser. No. 871,390 filed June 6, 1986 which itself is a continuation-in-part of U.S. Ser. No. 650,206 which is now U.S. Pat. No. 4,594,999.

BACKGROUND OF THE INVENTION

1. Field of the Invention

This invention relates in general to devices for immobilizing the human head, neck and torso and relates more particularly to such devices for use in emergency situations to immobilize the body to prevent further injury to the injured or potentially injured cervical spine. The device is especially useful for rescue at sea, or in other wet and/or snowy locations.

2. Description of the Prior Art

Numerous devices have been proposed in the past to perform the function of immobilizing or stabilizing the human head and neck for emergency purposes. Such devices are extremely important, particularly in emergency situations, in the handling of possible fractures of the cervical spine. In the cases of industrial injuries, automobile accidents and battlefield injuries, it is usually necessary to remove the patient from the injury scene, often under conditions of stress or time pressure, for transportation to medical facilities. This removal is almost always accomplished by personnel who are not medical doctors, although they may have had varying amounts of education and training in the handling of injured patients.

In the handling and moving, there is a high risk of aggravation of injuries to the cervical spine if the patient's head and neck are not properly immobilized or stabilized.

Many prior art U.S. Patents disclose devices comprising a rigid board member having straps attached thereto for attachment to a patient to immobilize the head and neck. These devices provide a rigid structure for completely preventing lateral motion and rotation of the patient's head but are expensive, bulky and complicated to use. Because of their cost, emergency personnel can usually afford to have only one device with them. This not only makes proper immobilization impossible of other injured patients in the same accident but also prevents the emergency personnel from returning to duty until their board is returned. Further, the board may not be removed until x-rays have ruled out neck or back injuries. The wood or metal devices presently used allow only very poor quality films when x-rays are shot through them.

Some of these problems were addressed in my first patent application, now U.S. Pat. No. 4,594,999. Others of these problems such as the need for an improved cervical immobilization board for use in wet conditions were not recognized at that time.

There is a need, therefore, for an optionally disposable, inexpensive readily stackable, more radiolucent C-spine immobilizer that can be employed easily by non-physician personnel.

It is an object to provide a cervical spine immobilizer that is easily and quickly applied to injured persons, and allows them to be carried while wearing the device.

Still another object is to provide a spine board that can be stored in large quantities in very little space, such as on shipboard.

Yet another object is to provide a light weight spine board that is suitable for wet disaster situations.

These and other objects of the invention will in part be obvious and will in part appear hereinafter.

The invention accordingly comprises the product possessing the features, properties and the relation of elements which are exemplified in the following detailed disclosure and the scope of the application of which will be indicated in the claims.

For a fuller understanding of the nature and objects of the invention, reference should be had to the following detailed description taken in connection with the accompanying drawings.

SUMMARY OF THE INVENTION

A cervical spine immobilization device is provided that comprises a corrugated plastic board member. The device includes a reinforcement panel at a critical central zone. Various portions of the device are held together in their secured locations by straps and belts such as of nylon webbing attached to the device.

The device is adapted for easy storage and use in emergency medical treatment situations, including underwater rescue efforts.

DESCRIPTION OF THE FIGURES

FIG. 1 is a front elevational view of the device of this invention.

FIG. 2 is a side elevation view thereof.

FIG. 3 is a top plan view.

FIG. 4 is a rear elevational view of the device of this invention.

DESCRIPTION OF THE PREFERRED EMBODIMENT

Figure 5:
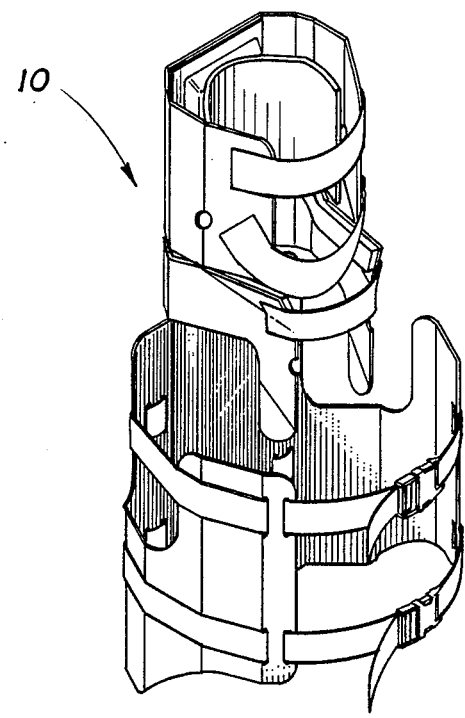
FIG. 5 is a side perspective view showing the strappings in their respective secured positions.

As seen in FIG. 1 device 10 has a main body portion 11 comprised of corrugated plastic in which the corrugations are vertically oriented for ease of fitting to patient which includes a generally longitudinal elongated center reinforcement portion 12 which is comprised of preferably a single thickness solid vacuum molded plastic which is then permanently mounted thereon as by stapling to the central section 11' of main body 11 with 1" metal staples. Preferably reinforcement 12 has rounded top and bottom edges 12B.

Depending outwardly at the top of main body 11 are head flanges 13 and 15. These are generally rectangular of optionally double thickness with preferably round upper corners 14 and lower corners 16. Disposed intermediate the head flanges at the top and the body members 25, 27 at the bottom of the device 10, are the neck collars 17, and 19 which are the next element to described.

Disposed just below said head flanges and also extending outwardly on either side of said center portion 12 are the neck collar members 17 and 19. Fold lines 33 and 35 which commence external to 12B, for the interior edge of both head flanges while the hard neck collar members 17 and 19 have fold lines designated 33' and 35', which are in fact segments of fold lines 33 and 35, as their interior edges. While designated fold lines, the folds will most likely transpire at time of usage.

Returning now to the discussion of the flanges, it is seen that the intermediate vertical fold lines 81 and 82 are spaced substantially equidistant from each other, and though by a greater distance from the outer vertical edge of each head flange to the outermost of said fold lines 81, 82, as well as equidistant from the respective interior fold lines 33 and 35. Optionally a throughbore 83, 84 may be made in the head flange of about 1" diameter, spaced up about 4" on the first inwardly intermediate fold line 81 and 82. These throughbores serve as a guide means for sound directed to the ears of the patient such that when the head flange is positioned as shown in FIG. 8, the patient can still hear, since sound will not easily penetrate the closed cell foam stabilizer which is designated 90 and is described below.

Slots 18 and 20, usually about ¼" in elevation, are situated between the bottom edge of each head flange and its adjacent collar member, to permit each to be used independently.

The neck collar members 17 and 19 comprise generally outwardly extending, mirror image, 90 degree downwardly depending, boot-like portions secured to or integrally formed with central member 11'. These include vertical fold lines 71 and 72. Portions 17 and 19 each include a built in triangular chin tab 51 and 52 within the upper distal corner relative to the central reinforcement portion 12. These chin tabs may be separately padded on the front surface, e.g. with a urethane foam layer or preferably as seen in FIG. 1, the pads extend full width across the upper edge thereof and are designated 251, 252. Diagonal score lines 55 and 56 are used to fold back these built in chin tabs 51 and 52 to conform to the bone structure of the patient. Note the angularity elsewhere in the Figures of the chin tab. The boot-like portions 17' and 19' also have rounded edges at the lower end thereof, again to avoid injury to the patient.

Figure 6:
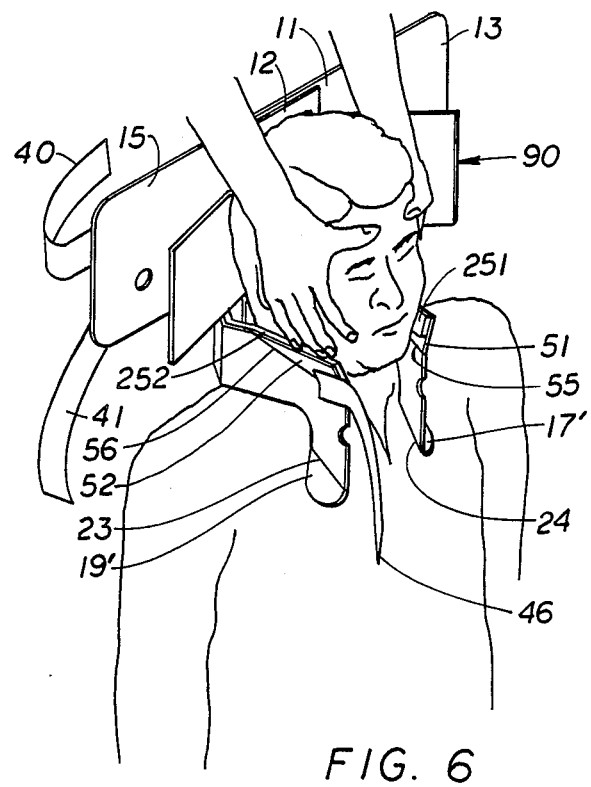
FIGS. 6, 7 and 8, are perspective views illustrating the use of the instant device to immobilize a human being.
Figure 7:
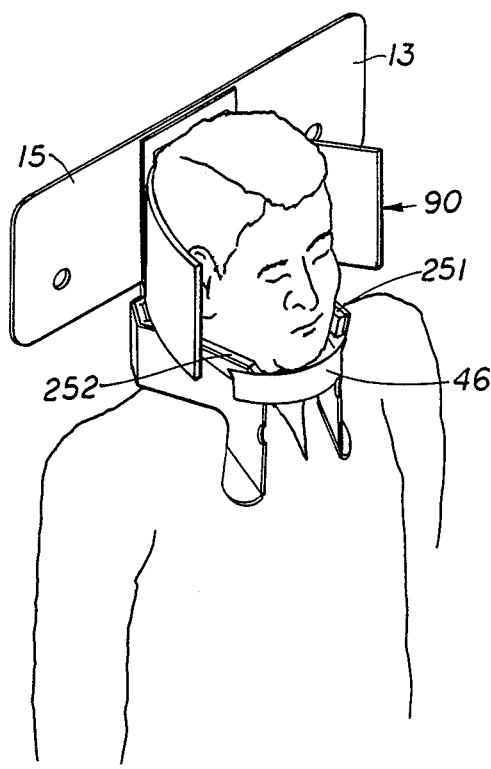
Figure 8:
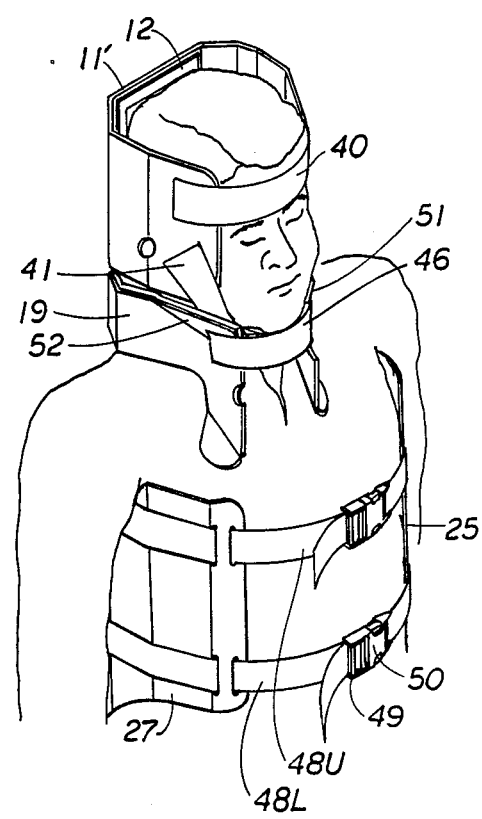

Lower score lines 23 and 24, are used in the positioning of the collar members 17 and 19 relative to the patient as seen in FIGS. 6–8.

In use, the lower score lines 23, 24 are bent outward to allow a flat surface to press against the patient's chest in order to complete the support of the collar members 17, 19.

Score lines are to be differentiated from fold lines in that score lines are diagonal, while fold lines are vertical as used herein.

An optional, but preferred hemispherical cutout 29 may be made on the edge of the members 17 and 19 to permit an easy wide access to the throat should a tracheotomy be necessary.

As will be understood on reading the area below pertaining to use of this invention, the disposition of the collar is key, since it serves to center the board 10 on the patient in contrast to virtually every other vest type spinal immobilization device wherein the patient is centered by the body flanges.

The discussion now turns to the body members 25 and 27, per FIG. 1. These single thickness body members 25 and 27 are each disposed on opposite sides of the central section 11' and are preferably integrally formed therewith since they too are made of double walled corrugated plastic, preferably the same plastic material as to the head flanges and collar members preferably with the corrugations vertically oriented.

Body members 25 and 27 each include several segments. The first of these are L-shaped, outwardly extending mirror image segments 25A and 27A which are disposed adjacent to the central section 11' as reinforced by elongated member 12. Each of these segments extends outwardly to a vertical fold line 61B and 62B respectively.

The intermediate fold lines 61C and 62C respectively are vertically aligned with a pair of the exterior intermediate fold lines 81 and 82 on head flanges 15 and 13 respectively.

The wing segments 25B and 27B commence along the fold lines 61B and 62B and comprise two parts. The first parts are each quadrilaterals, 125B and 127B and each extends from along fold line 61B and 62B respectively, generally outward and then upward and convexly arcuate from the bottom edge 37, 36 of the shorter in elevation part of the L-shaped segments to fold lines 61A and 62A respectively, as well as outwardly and then concavely arcuate upward from the top edge 39, 38 of the shorter in elevation part of the L-shaped segments to fold lines 61A and 62A; to their terminal also at fold line 61A and 62A, which fold lines constitute the intersections of the second part of the wing segments, 225B and 227B. These wing segment second parts 225B and 227B are each generally rectangular with each of the three corners being preferably rounded for the comfort of the patient. Vertical fold line 61A' and 62A' are spaced inwardly from the outer edge of the second segments, i.e. fold lines 61A and 62A. Having described the structure in general, the discussion now turns to the elements used to secure the patient within the device. The actual mode to do so will be discussed infra. Reference is now made to FIG. 4 as well as to FIG. 1.

Since FIG. 1 is the larger figure, the plurality of elongated slots for the threading of the single layer webbing belts is shown with their appropriate numerical designator. To keep the 4th figure from being cluttered, only the straps and belts have been numbered, and not the slots. It is to be seen however that the strapping used for the Velcro connections, as around the head, constitutes two layered strapping.

As is known, Velcro is a registered trademark of Velcro USA for its patented engageable and releasable multihook cloth closure. The closure employs a male hooking section and a female hook receiving section.

The head flanges 13, 15 are secured by two vertically spaced velcro straps 40 and 41 each of which is two layered. The first layer is a nylon or polyolefin on the rear, i.e. the surface designated 43, while the front face has a co-extensive pile type layer thereupon designated 42. Each of these straps 40, 41, is engageable with its respective vertically spaced rock type tab 45 and 44, which tabs are horizontally axially aligned with their respective straps.

The neck collar members are secured by a single similar Velcro pile type strap 46 which engages a single Velcro hook type tab 47, after the members have been bent from a first extended position, through a second parallel position, to a third position facing each other over the upper chest of the victim (wearer), with the area beneath the score lines 23 and 24 bent outwardly.

It is to be seen that a male Velcro section can be substituted for the female on the strap and that the tab can be female, since the same closure interlock will transpire. Also, there is no criticality as to left or right for the disposition of the tabs and straps. Any and all of the straps may be on the left side of the rear of the device 10 or on the right rear thereof, so long as the tab is placed in the counterpart location. Caution should be exercised because Velcro hooks stick to anything and are abrasive on the skin.

Sets of two pairs of vertically elongated horizontally and vertically aligned slots designated 95AU, 95BU, 95AL, 95BL, 96AU, 96BU, 96AL, and 96BL respectively are provided in the second segments 27B and 25B.

A second set of pairs of vertically and horizontally similarly sized vertically elongated slots 97AU, 97BU, 97AL, 97BL, 98AU, 98BU, 98AL & 98BL are provided in the L-shaped segments between fold lines 61C and 33; and between fold lines 62C and 35 respectively laterally. The second two pair of slots should be horizontally aligned with the respective upper and lower first two pair of slots, in order to receive webbing belts, to be described else where herein.

In the nomenclature pertaining to elongated slots 95 through 98 inclusive, "A" designates the outer of the two slots, and "B" the inner; while "U" and "L" designate upper or lower position.

The belts are made of nylon or polyolefin webbing and are similar to those used for automobile or airplane seat belts. Thus belts 48U and 48L (upper and lower) are threaded through the pairs of aligned elongated slots as described previously for proper disposition. The height of the slots 95AU, 95BU, 95AL, 95BL are large enough such that the belts 48 can be disposed in place with the tongue 49 and receptor 50 in place at opposite ends of each belt. Any type of conventional tongue and appropriate receptor available in the marketplace may be employed. Complete belts 48 including the tongue and receptor are readily available from several manufacturers.

Also seen in FIG. 4 are a pair of vertically aligned slots which are both wider and longer than the slots discussed above. These slots 37,38 are designed as hand holds and are sized to receive an average human hand. A hand of an ambulance team member is placed in each hand hold 37, 38, during the positioning of the patient onto a stretcher, to avoid slippage due to the inherent slippery nature of the plastic material employed in the construction of device 10.

The tabs and straps may be secured in place by any conventional means, e.g. glue, staples, stitching or a combination thereof.

Returning now to the reinforcement member 12, as seen in FIG. 1, which is held in place by staples, and/or adhesive, there is superposed thereon a closed cell foam head stabilizer 90. This head stabilizer is a U-shaped member having a central portion 91 secured as by a suitable adhesive to reinforcement member 12 adjacent rounded upper edge 12B and between 12B and the bottom of the recess 12C on 12. Extending outwardly therefrom on opposite sides are a pair 92, 93 of extension sections that are integrally formed with central portion 91 and extend generally forward. The extension sections serve both to cushion and to better hold the head of the user in position when the head flaps are folded up around the head as shown in the drawings. The head stabilizer provides both comfort to the face and retention within the head flaps 15, 14.

Upper surface 12C is an optional recess that receives and comforts the back of the head. See FIG. 1.

DISPOSITION UPON AN INJURED PARTY

While the device can be positioned on a patient by a single rescuer, the use of two persons who are adequately trained in C-spine immobilization techniques is recommended.

First, position the collar as shown in FIG. 6. This is achieved by bending the chin tabs 51 and 52 back at the pre-scored cuts 56 and 55 per FIG. 1 and FIGS. 4–6. The small rubber pads 252 and 251 seen in FIG. 1, are to be placed just under the outer edges of the jaw per FIG. 6. If necessary bend the lower portion of the collar outward as needed to keep the neck of the patient in a neutral position. The pair of head straps 40, 41, which have pile type Velcro thereon are brought over into engagement with the hook type Velcro tabs 45 and 44 neither of these last mentioned tabs being visible in FIG. 8, but which are seen in FIG. 4.

Next, bring the pile type strap 46 into engagement with the hook tab 45 adjusting for patients size.

Thirdly, the straps 48U and 48L are adjusted to accommodate the girth of the patient, by moving the tongue ends 49 along their respective belts such that the tongues can engage the receivers 50 to thereby retain the patient within the confines of the body member segments. Reference is made to FIG. 8.

As a caution, the rescuers are advised to make sure that there is no pressure being applied against the trachea or the carotid arteries or throat. One reason for elements 251 and 252 is to help avoid such pressure.

The instant device is intended for either a one time usage, after which it can be discarded, due to its relatively low cost or if desired it can be used a multiplicity of times, since it is strong enough to permit same. In view of the materials employed herein, while the device is not primarily intended to be used for the vertical lifting of a sitting patient, nor for the dragging of an injured party from the scene of an incident as by pulling on the device, it may be used for such purposes on a limited basis if necessary.

The corrugated double walled plastic board recommended for this device need not be dipped sprayed or otherwise coated with a waterproofing agent such as a wax or plastic coating, since the plastic layers used herein is itself is waterproof, as is the webbing used for the strapping.

Printed indicia such as instructions, product safety information and the like can be printed at various locations such as those marked 58.

The device of this invention, which is preferably made, except as noted, primarily from high density polyethylene corrugated plastic sheeting overlaid on each side with high density non-corrugated reinforcing panels is seen to provide the dual benefit of both C-spine immobilization, as well as providing a built in hard cervical collar to rigidity the head of an injured patient, when secured to the body using the straps as disclosed herein.

Since certain changes may be made in the above article without departing from the scope of the invention herein involved, it is intended that all matter contained in the above description and shown in the accompanying drawings shall be interpreted as illustrative and not in a limiting sense.

I claim:
1. An optionally reuseable cervical spine board device adapted to restrain the head and body of an injured person comprising

(A) a main body portion, having a central section and a flat, elongated, centrally disposed reinforcement portion of a rectangular configuration, of an elevation equal to that of a main body, mounted on said central section,
and a head stabilizer superposed on said reinforcement portion;

(B) a pair of head flanges, one of which extends outwardly on either side of said central section and which flanges are capable of moving from a first position in the same plane as said central section to a second position generally normally upward from said central section, (C) a hard neck collar comprising
a pair of neck collar members one on each side of the central portion, also extending outwardly from said central section and extending further than said head flanges, movable from the same first position through a second position to a third position substantially parallel to each other,
each neck collar member having a built in outwardly foldable chin tab, (D) a pair of body members, one on each side of said central section, said body members including a first L-shaped segment adjacent to said central section and a wing segment capable of moving from a first position in the same axis as the central section upwardly and inwardly toward the other of said wing segments to a spaced relationship second position opposed to the other of said wing members;

(E) means for securing said head flanges to each other and for securing said neck collar members to each other the former in their second position, the latter in their third position.

2. In the device of claim 1 wherein a fold line separates each L-shaped body member segment from its respective wing member.

3. In the device of claim 1 wherein each wing member has a right angle notched corner.

4. In the device of claim 1 wherein the collar members have a descending section with a hemispherical cut out on the exterior edge thereof.

5. In the device of claim 1 wherein a fold line separates the head flanges and the collar member from the central section.

6. In the device of claim 1 wherein the collar members each include a foldable built in chin tab orientable to a position different from the disposition of the balance of said collar members.

7. In the device of claim 6 wherein the device is constituted of double walled, corrugated plastic, main body portion, except the attached centrally disposed reinforcement portion.

8. In the device of claim 1 wherein each head flange includes a throughbore to serve as a sound director.

9. In the device of claim 6 wherein the chin tabs also include padding on the front surface thereof.

10. In the device of claim 1 wherein each body member has a sinusoidally curved top edge spaced down from its respective collar member and slots adapted to receive at least one belt for securing said body members to each other, and at least one belt in said slots, said at least one belt having a tongue and receptor.

11. In the device of claim 10 wherein the body members have a notched lower, outer corner, and the number of belts is two.

12. In the device of claim 1 wherein the head flanges are rounded at their corners and include a plurality of horizontally spaced vertical fold lines.

13. In the device of claim 1 wherein the collar members extend outward from said central section more than said head flanges but less than said body members.

14. In the device of claim 12 wherein the collar members include webbing means, which webbing means include a hook or pile tab on the rear of one said collar members, and an engageable therewith strap extending outwardly horizontally from the other of said collar members, said strap having a hook or pile surface engageable with said hook or pile tab.

15. In the device of claim 12 wherein the collar members also include a plurality of horizontally spaced vertical fold lines, and the reinforcement member is of slightly less elongation than the central section of the main body portion.

16. In the device of claim 15 wherein the collar members each include an exterior edge with a hemispherical cut out, and a foldable padded built in chin tab, and the reinforcement member has rounded top and bottom edges.

17. In the device of claim 16 wherein the body members have a plurality of horizontally spaced vertical fold lines.

18. In the device of claim 1 wherein the central section of said main body portion includes a pair of spaced vertically elongated hand hold slots.

19. The device of claim 14, wherein the webbing means to secure said head flanges comprises a pair of straps each having a hook or pile surface thereupon, each attached to one of said headflaps, and a pair of hook or pile tabs, one engageable with each of said straps, mounted on the other of said head flanges.

20. The device of claim 10, wherein the number of belts to secure said body members is two, and wherein each collar member is secureable to the other by the engagement of a hook or pile surfaced strap disposed to extend laterally from one of said collar members, and a hook or pile tab disposed on the other of said collar members.

21. The device of claim 1 wherein the head stabilizer is a U-shaped member, the central section of which is secured to said reinforcement member, said U-shaped member having an extension portion on each side thereof, which extension portions extend generally forwardly from said central section.

22. The device of claim 20 wherein the head stabilizer is a U-shaped member, the central portion of which is secured to said reinforcement member, said U-shaped member having an extension portion on each side thereof, which extension portions extend generally forwardly from said central section.

* * * * *